US009637517B2

United States Patent
Mi et al.

(10) Patent No.: US 9,637,517 B2
(45) Date of Patent: May 2, 2017

(54) METHOD FOR PREPARING EXENATIDE (71) Applicant: HYBIO PHARMACEUTICAL CO., LTD., Shenzhen (CN)

(72) Inventors: Pengcheng Mi, Shenzhen (CN); Jian Liu, Shenzhen (CN); Yaping Ma, Shenzhen (CN); Jiancheng Yuan, Shenzhen (CN)

(73) Assignee: HYBIO PHARMACEUTICAL CO., LTD., Shenzhen (CN)

( * ) Notice: Subject to any disclaimer, the term of this patent is extended or adjusted under 35 U.S.C. 154(b) by 77 days.

(21) Appl. No.: 14/371,004

(22) PCT Filed: Oct. 31, 2012

(86) PCT No.: PCT/CN2012/083795
§ 371 (c)(1),
(2) Date: Jul. 8, 2014

(87) PCT Pub. No.: WO2014/067084
PCT Pub. Date: May 8, 2014

(65) Prior Publication Data
US 2015/0232503 A1    Aug. 20, 2015

(51) Int. Cl.
C07K 1/04    (2006.01)
C07K 14/00   (2006.01)

(52) U.S. Cl.
CPC .............. *C07K 1/04* (2013.01); *C07K 14/001* (2013.01)

(58) Field of Classification Search
None
See application file for complete search history.

(56) References Cited

U.S. PATENT DOCUMENTS

| | | | |
|---|---|---|---|
| 6,251,583 B1 | 6/2001 | Zhang et al. |
| 6,902,744 B1 | 6/2005 | Kolterman et al. |
| 6,924,264 B1 | 8/2005 | Prickett et al. |
| 7,157,555 B1 | 1/2007 | Beeley et al. |

FOREIGN PATENT DOCUMENTS

| | | | |
|---|---|---|---|
| CN | 101357938 | 2/2009 | |
| CN | 101538324 | 9/2009 | |
| CN | 101790538 | 7/2010 | |
| CN | 102655883 | 9/2012 | |
| EP | 1773870 | * 12/2009 | ........... C07K 14/575 |

OTHER PUBLICATIONS

Novabiochem Mar. 2002 Catalog, p. i-29, 4.5 and 4.6.*
Applied Biosystems Technical Bulletin, "Cleavage, Deprotection, and Isolation of Peptides after Fmoc Synthesis" (May 1998) 1-12.*
Google translation of CN101538324, obtained on Sep. 11, 2015.*
English translation of PCT International Search Report issued in International Patent Application No. PCT/CN2012/083795, dated Aug. 15, 2013.
Colombo, "A new solid-phase synthesis of porcine vasoactive intestinal peptide using N(alpha)-9-fluorenylmethyloxycarbonyl amino acids," *Experientia*, 38:773-775, 1982.
Extended European Search Report issued in European Application No. 12887604.2, dated May 11, 2016.

* cited by examiner

*Primary Examiner* — Marcela M Cordero Garcia
*Assistant Examiner* — Catherine Mader
(74) *Attorney, Agent, or Firm* — Parker Highlander PLLC (57) ABSTRACT

Disclosed in the present invention is a method for preparing Exenatide. Serine resin is obtained through a first coupling of serine and resin and successively with amino acids through a second coupling to obtain a peptide resin with a sequence as shown by SEQ ID No. 1; Exenatide resin is obtained through a third coupling of histidine containing a protecting group or salts thereof and the peptide resin with a sequence as shown by SEQ ID No. 1, then it is cracked and purified to obtain purified Exenatide peptide. The method for preparing Exenatide of the present invention inhibits the formation of D-His-Exenatide, and thereby improves the yield and purity of Exenatide.

6 Claims, 1 Drawing Sheet

METHOD FOR PREPARING EXENATIDE

This application is a national phase application under 35 U.S.C. §371 of International Application No. PCT/CN2012/083795, filed Oct. 31, 2012. The entire content of the above referenced disclosure is specifically incorporated herein by reference.

The sequence listing that is contained in the file named "UNITP0005US_ST25.txt", which is 2 KB (as measured in Microsoft Windows®) and was created on Jun. 25, 2014, is filed herewith by electronic submission and is incorporated by reference herein.

FIELD OF THE INVENTION

The present invention relates to the field of polypeptide synthesis, and particularly, to a method for the preparation of exenatide.

BACKGROUND OF THE INVENTION

Diabetes is a series of metabolism disorder syndromes of sugar, protein, lipid, water, electrolyte and the like, due to hypoinsulinism, insulin resistance and the like, resulted from the action of various pathogenic factors on the body, including hereditary factors, immune disorder, microbiological infection and the toxins thereof, free radical toxins and psychic factors etc. Clinically, diabetes is mainly characterized by hyperglycemia, in which manifestations, such as diuresis, polydipsia, polyphagia and emaciation (i.e., "three enhancements and one reduction" in symptoms) etc. may appear in typical cases. Once diabetes (blood sugar) is not well controlled, complications may occur, which result in incurable failure and lesions in kidney, eye and foot.

Diabetes can be divided into type I diabetes, type II diabetes, gestational diabetes and other special types of diabetes. Type II diabetes accounts for about 95% of all the diabetic patients. Type I diabetes is a kind of autoimmune disease, resulted from the attack on the body by the immune system itself. The pancreatic beta cells of the diabetic patient, by which insulin is secreted, are attacked and killed by his own immune system, leading to insufficient insulin secreted by the pancreas. Type I diabetes mostly occurs in adolescents, who will rely on exogenous insulin supplemented to maintain their lives, due to the lack of insulin secreted. Type II diabetes exhibits stronger heritability and environmental factors, and has significant heterogeneity. At present, it is believed that the pathogenesis of diabetes is a combination of insulin resistance (mainly manifested as hyperinsulinemia and low glucose utilization) and hypoinsulinism, and as a result, the manifestations of diabetes are not always the same, in which in some cases insulin resistance dominates accompanied with hypoinsulinism, while in other cases hypoinsulinism dominates accompanied with or without insulin resistance.

Exenatide, as shown in Formula I, has an amino acid sequence of SEQ ID No. 2, which is the first incretin analog developed by Eli Lilly and Company (USA) together with Amylin Company. Exenatide is a synthetic polypeptide composed of 39 amino acids, which has similar effects as an endogenous incretin such as glicetin-1 (GLP-1), including promoting glucose-dependent insulin secretion, restoring first-phase insulin secretion, inhibiting glucagon secretion, slowing the evacuation of gastric contents, and improving the function of pancreatic beta cells. In 2004, exenatide has been approved for marketing by FDA under the trade name Byetta. It is a subcutaneous injection formulation administrated twice a day.

The application has been approved by US Food and Drug Administration (FDA) on Jan. 27, 2012 for marketing of the controlled release formulation (once a week) of exenatide injection. The control of blood sugar can be improved by using such a formulation for adult patients of type II diabetes on the basis of diet and exercise. This is the first therapeutic drug for type II diabetes administered weekly.

This peptide was synthesized by single solid-phase sequential coupling methods as described in U.S. Pat. No. 6,924,264, U.S. Pat. No. 7,157,555, U.S. Pat. No. 6,902,744 and CN101357938A. Using amine resin as the carrier, exenatide was obtained by sequential coupling and final cleavage. However, since the amino acid at the N-terminal is His, racemic impurities of His, which is difficult to be removed by purification, may be created by using the routine coupling material Fmoc-His(Trt)-OH and the coupling methods in the Fmoc solid phase synthesis.

Formula I

SUMMARY OF THE INVENTION

On such a basis, there is provided a method for the preparation of exenatide in the present invention. In this method, the yield and purity of exenatide are improved by adopting protective group-containing histidine or a salt thereof and fragment synthesis method, based on the inhibition of D-His-exenatide production.

In order to achieve the above object of the present invention, the present invention provides the following technical solutions:

A method for the preparation of exenatide is provided in the present invention, comprising the following steps:

Step 1: serine-resin is obtained by a first coupling between serine and resin;

Step 2: peptide-resin of SEQ ID No. 1 is obtained by a second coupling of said serine-resin sequentially with amino acids;

Step 3: exenatide-resin is obtained by a third coupling between the protective group-containing histidine or a salt thereof with said peptide-resin of SEQ ID No. 1, and exenatide is finally obtained after cleavage and purification.

Preferably, the protective group-containing histidine or a salt thereof in step 3 has the structure as shown in formula II:

X-His(Y)—OH   Formula II wherein, X is selected from the group consisting of Fmoc, Boc and Trt; and
Y is selected from the group consisting of Trt, Bum, Boc, mtt and mmt.

Preferably, the protective group-containing histidine or a salt thereof in step 3 has the structure as shown in formula III X-His(Boc)-OH   Formula III wherein, X is selected from the group consisting of Fmoc, Boc and Trt.

Preferably, the protective group-containing histidine or a salt thereof in step 3 has the structure as shown in formula IV Boc-His(Boc)-OH.DCHA   Formula IV Preferably, the third coupling is pre-activated coupling or in-situ coupling.

Preferably, particularly in step 3, exenatide-resin is obtained in a solvent in the presence of a coupling agent and an organic base via the third coupling between the protective group-containing histidine or a salt thereof with said peptide-resin of SEQ ID No. 1, and exenatide is finally obtained after cleavage by a cleaving agent and purification.

Preferably, the coupling agent is HATU and HOAt.
Preferably, the organic base is DIPEA or TMP.
Preferably, the solvent is one of NMP, DMF and DCM, or a mixture of two or more thereof.
Preferably, the cleaving agent is a mixture of TFA, PhSMe, EDT, TIS, water and phenol.
Preferably, the volume ratio of TFA, PhSMe, EDT, TIS, water and phenol in the cleaving agent is 80-85:2-5:2-5:2-5:0-3:0-2.
Preferably, the reaction temperature of the third coupling is in the range from 0 to 30° C.
Preferably, particularly in step 2, peptide-resin of SEQ ID No. 1 is obtained in a solvent in the presence of a coupling agent and an organic base via the second coupling of said serine-resin sequentially with amino acids.

Preferably, the coupling agent is HATU or HOAt.
Preferably, the organic base is DIPEA or TMP.
Preferably, the solvent is one of NMP, DMF and DCM, or a mixture of two or more thereof.
Preferably, particularly in step 2, peptide-resin of SEQ ID No. 1 is obtained via the second coupling of said serine-resin sequentially with Fmoc-Pro-OH, Fmoc-Pro-OH, Fmoc-Pro-OH, Fmoc-Ala-OH, Fmoc-Gly-OH, Fmoc-Ser(tBu)-OH, Fmoc-Ser(tBu)-OH, Fmoc-Pro-OH, Fmoc-Gly-OH, Fmoc-Gly-OH, Fmoc-Asn(Trt)-OH, Fmoc-Lys(Boc)-OH, Fmoc-Leu-OH, Fmoc-Trp(Boc)-OH, Fmoc-Glu(OtBu)-OH, Fmoc-Ile-OH, Fmoc-Phe-OH, Fmoc-Leu-OH, Fmoc-Arg(pBf)-OH, Fmoc-Val-OH, Fmoc-Ala-OH, Fmoc-Glu(OtBu)-OH, Fmoc-Glu(OtBu)-OH, Fmoc-Glu(OtBu)-OH, Fmoc-Met-OH, Fmoc-Gln(Trt)-OH, Fmoc-Lys(Boc)-OH, Fmoc-Ser(tBu)-OH, Fmoc-Leu-OH, Fmoc-Asp(OtBu)-OH, Fmoc-Ser(tBu)-OH, Fmoc-Thr(tBu)-OH, Fmoc-Phe-OH, Fmoc-Thr(tBu)-OH, Fmoc-Gly-OH, Fmoc-Glu(OtBu)-OH, Fmoc-Gly-OH.

Preferably, the reaction temperature of the second coupling is in the range from 0 to 30° C.
Preferably, the coupling agent for the first coupling is HOBt.
Preferably, the reaction temperature of the first coupling is in the range from 0-30° C.
Preferably, the resin in step 1 is Rink Amide-MBHA Resin.

There is provided a method for the preparation of exenatide in the present invention. In this method, exenatide is synthesized by adopting protective group-containing histidine or a salt thereof using an in-situ synthesis or a pre-activation method. Particularly, serine-resin is obtained by a first coupling between serine and resin; subsequently, peptide-resin of SEQ ID No. 1 is obtained by a second coupling of said serine-resin sequentially with amino acids; and exenatide-resin is then obtained by a third coupling between the protective group-containing histidine or a salt thereof with said peptide-resin of SEQ ID No. 1, and purified exenatide is finally obtained after cleavage and purification. Based on the inhibition of D-His-exenatide production, the yield and purity of exenatide are improved by the preparation method of exenatide provided herein.

DETAILED DESCRIPTION OF THE INVENTION

A method for the preparation of exenatide is disclosed by the present invention, which can be implemented by properly modifying the processing parameters by those skilled in the art with reference to the content disclosed herein. Particularly, it should be noted that all similar replacements and modifications are apparent to those skilled in the art, all of which are regarded to be included in the present invention.

The method of the present invention and the applications thereof will be described by preferred Examples, and it is apparent that modification, or proper change and the combination thereof can be made to the method and applications described herein by those skilled in the art, without departing from the content, spirit and scope of the invention, in order to achieve and apply the techniques disclosed in the present invention.

| Abbreviation | Full form |
| --- | --- |
| DCHA | Dicyclohexylamine |
| CHA | Cyclohexylamine |
| Bum | T-Butoxymethyl |
| mmt | 4-methoxytrityl |
| mtt | Methyl trityl |
| Trt | Trityl |
| HOAt | 1-hydroxy-7-azobenzotriazole |
| Fmoc | 9-fluorenylmethyloxycarbonyl |
| DIPCDI | Diisopropyl carbodiimide |
| HOBt | 1-hydroxybenzotrizole |
| HATU | 2-(7-azo-benzotriazole)-N,N,N',N'-tetramethyluronium hexafluorophosphate |
| HBTU | Benzotriazole-N,N,N',N'-tetramethyluronium hexafluorophosphate |
| DIPEA | N,N-diisopropylethylamine |
| DMF | N,N-dimethyl formamide |
| DCM | Dichloromethane |
| NMP | N-methyl pyrrolidone |
| TMP | 2,4,6-Trimethylpyridine |
| TFA | Trifluoroacetic acid |
| PhSMe | Thioanisole |
| TIS | Triisopropylsilane |
| EDT | Ethanedithiol |
| Phenol | Phenol |
| SCX-HPLC | Strong cation-exchange chromatography |

Example 1

Synthesis of Fmoc-Ser(tBu)-Rink Amide-MBHA Resin with a Substitution Degree of 0.1 mmol/g 100 g Rink Amide-MBHA resin was weighed and added to the solid-phase reaction column followed by washing with DMF twice. After the resin was swollen in DMF for 30 minutes, the Fmoc protection was removed by DBLK and the resin was washed by DMF for 6 times. The resin was tested by ninhydrin test, in which the removal of Fmoc was indicated by the coloring developed in the resin. 4.60 g Fmoc-Ser(tBu)-OH (12 mmol) and 1.95 g HOBt (14.4 mmol) were weighed and dissolved in a mixed solution of DCM and DMF in a volume ratio of 1:1. After activation for 3 min by adding 2.25 ml DIC (14.4 mmol) in an ice water bath, the solution was added to the solid-phase reaction column and reaction was performed at room temperature for 2 h. The resin was washed with DMF for 3 times, and the blocking solution (pyridine/acetic anhydride=1:1) was added for blocking for 2 h. The resin was washed with each of DMF and DCM for 4 times, shrunk in methanol and methanol was removed to dry by sucking, Fmoc-Ser(tBu)-Rink Amide-MBHA resin was obtained. The substitution degree was determined as 0.098 mmol/g.

Example 2

Synthesis of Fmoc-Ser(tBu)-Rink Amide-MBHA Resin with a Substitution Degree of 0.2 mmol/g 100 g Rink Amide-MBHA resin was weighed and added to the solid-phase reaction column followed by washing with DMF twice. After the resin was swollen in DMF for 30 minutes, the Fmoc protection was removed by DBLK and the resin was washed by DMF for 6 times. The resin was tested by ninhydrin test, in which the removal of Fmoc was indicated by the coloring developed in the resin. 9.20 g Fmoc-Ser(tBu)-OH (24 mmol) and 3.89 g HOBt (28.8 mmol) were weighed and dissolved in a mixed solution of DCM and DMF in a volume ratio of 1:1. After activation for 3 min by adding 4.50 ml DIC (28.8 mmol) in an ice water bath, the solution was added to the solid-phase reaction column and reaction was performed at room temperature for 2 h. The resin was washed with DMF for 3 times, and the blocking solution (pyridine/acetic anhydride=1:1) was added for blocking for 2 h. The resin was washed with each of DMF and DCM for 4 times, shrunk in methanol and methanol was removed to dry by sucking, Fmoc-Ser(tBu)-Rink Amide-MBHA resin was obtained. The substitution degree was determined to be 0.192 mmol/g.

Example 3

Synthesis of Fmoc-Ser(tBu)-Rink Amide-MBHA Resin with a Substitution Degree of 0.3 mmol/g 100 g Rink Amide-MBHA resin was weighed and added to the solid-phase reaction column followed by washing with DMF twice. After the resin was swollen in DMF for 30 minutes, the Fmoc protection was removed by DBLK and the resin was washed by DMF for 6 times. The resin was tested by ninhydrin test, in which the removal of Fmoc was indicated by the coloring developed in the resin. 13.8 g Fmoc-Ser(tBu)-OH (36 mmol) and 5.84 g HOBt (43.2 mmol) were weighed and dissolved in a mixed solution of DCM and DMF in a volume ratio of 1:1. After activation for 3 min by adding 6.75 ml DIC (43.2 mmol) in an ice water bath, the solution was added to the solid-phase reaction column and reaction was performed at room temperature for 2 h. The resin was washed with DMF for 3 times, and the blocking solution (pyridine/acetic anhydride=1:1) was added for blocking for 2 h. The resin was washed with each of DMF and DCM for 4 times, shrunk in methanol and methanol was removed to dry by sucking, Fmoc-Ser(tBu)-Rink Amide-MBHA resin was obtained. The substitution degree was determined to be 0.302 mmol/g.

Example 4

Synthesis of Peptide-Resin of SEQ ID No. 1

78.1 g Fmoc-Ser(tBu)-Rink Amide-MBHA resin with a substitution degree of 0.192 mmol/g was weighed and added to the solid-phase reaction column. Subsequently, the resin was washed twice using DMF, and swollen in DMF for 30 min. Fmoc protection was removed by DBLK, and the resin was then washed for 6 times using DMF. The resin was tested by ninhydrin test, in which the removal of Fmoc was indicated by the coloring developed in the resin. 20.24 g Fmoc-Pro-OH (60 mmol) and 9.73 g HOBt (72 mmol) were weighed and dissolved in a mixed solution of DCM and DMF in a volume ratio of 1:1. After activation for 3 min by adding 11.26 ml DIC (72 mmol) in an ice water bath, the solution was added to the solid-phase reaction column and reaction was performed at room temperature for 2 h. The endpoint of the reaction was determined by ninhydrin test, in which the colorless and transparent resin indicated a complete reaction; while the coloring developed in the resin indicated an incomplete reaction, for which a further hour reaction was required. Such criteria were applied to the endpoint determination by ninhydrin test herein below. The coupling of 2-39 fragment was accomplished sequentially from C-terminal to N-terminal according to the backbone sequence of exenatide by repeating the above step of removing the Fmoc protection and the step of coupling with corresponding amino acid added. After the reaction was finished, the resin was shrunk in methanol and dried under vacuum over night, resulting in 160.3 g exenatide (2-39)-Rink Amide-MBHA resin by weighing.

Example 5

Synthesis of Peptide-Resin of SEQ ID No. 1

153.1 g Fmoc-Ser(tBu)-Rink Amide-MBHA resin with a substitution degree of 0.098 mmol/g was weighed and added to the solid-phase reaction column. Subsequently, the resin was washed twice using DMF, and swollen in DMF for 30 min. Fmoc protection was removed by DBLK, and the resin was then washed for 6 times using DMF. The resin was tested by ninhydrin test, in which the removal of Fmoc was indicated by the coloring developed in the resin. 20.24 g Fmoc-Pro-OH (60 mmol) and 9.73 g HOBt (72 mmol) were weighed and dissolved in a mixed solution of DCM and DMF in a volume ratio of 1:1. After activation for 3 min by adding 11.26 ml DIC (72 mmol) in an ice water bath, the solution was added to the solid-phase reaction column and reaction was performed at room temperature for 2 h. The endpoint of the reaction was determined by ninhydrin test, in which the colorless and transparent resin indicated a complete reaction; while the coloring developed in the resin indicated an incomplete reaction, for which another 1 h reaction was required. Such criteria were applied to the endpoint determination by ninhydrin test herein below. The coupling of 2-39 fragment was accomplished sequentially from C-terminal to N-terminal according to the backbone sequence of exenatide by repeating the above step of removing the Fmoc protection and the step of coupling with corresponding amino acid added. After the reaction was finished, the resin was shrunk in methanol and dried under vacuum over night, resulting in 233.9 g exenatide (2-39)-Rink Amide-MBHA resin by weighing.

Example 6

Synthesis of Peptide-Resin of SEQ ID No. 1

49.7 g Fmoc-Ser(tBu)-Rink Amide-MBHA resin with a substitution degree of 0.302 mmol/g was weighed and added to the solid-phase reaction column. Subsequently, the resin was washed twice using DMF, and swollen in DMF for 30 min. Fmoc protection was removed by DBLK, and the resin was then washed for 6 times using DMF. The resin was tested by ninhydrin test, in which the removal of Fmoc was indicated by the coloring developed in the resin. 20.24 g Fmoc-Pro-OH (60 mmol) and 9.73 g HOBt (72 mmol) were weighed and dissolved in a mixed solution of DCM and DMF in a volume ratio of 1:1. After activation for 3 min by adding 11.26 ml DIC (72 mmol) in an ice water bath, the solution was added to the solid-phase reaction column and reaction was performed at room temperature for 2 h. The endpoint of the reaction was determined by ninhydrin test, in which the colorless and transparent resin indicated a complete reaction; while the coloring developed in the resin indicated an incomplete reaction, for which another 1 h reaction was required. Such criteria were applied to the endpoint determination by ninhydrin test herein below. The coupling of 2-39 fragment was accomplished sequentially from C-terminal to N-terminal according to the backbone sequence of exenatide by repeating the above step of removing the Fmoc protection and the step of coupling with corresponding amino acid added. After the reaction was finished, the resin was shrunk in methanol and dried under vacuum over night, resulting in 131.3 g exenatide (2-39)-Rink Amide-MBHA resin by weighing.

Example 7

Synthesis of the Peptide-Resin of SEQ ID No. 2 by In-Situ Coupling Method Using Boc-His(Boc)-OH.DCHA and the Peptide-Resin of SEQ ID No. 1

15 mmol of the peptide-resin of SEQ ID No. 1 prepared in Example 4 was weighed and added to the solid-phase reaction column. The resin was washed twice with DMF, and swollen in DMF for 30 min. 32.22 g Boc-His(Boc)-OH.DCHA (60 mmol), 22.81 g HATU (60 mmol), 9.80 g HOAt (72 mmol) were added to the resin followed by addition of 500 ml NMP solution. After stirring for 5 min, 15.86 ml TMP (120 mmol) was added dropwise, and reaction was performed at 0° C. for 3 h. The endpoint of the reaction was determined by ninhydrin test, in which the colorless and transparent resin indicated a complete reaction; while the coloring developed in the resin indicated an incomplete reaction, for which a further hour of coupling reaction was required.

Example 8

Synthesis of the Peptide-Resin of SEQ ID No. 2 by In-Situ Coupling Method Using Boc-His(Boc)-OH.DCHA and the Peptide-Resin of SEQ ID No. 1

15 mmol of the peptide-resin of SEQ ID No. 1 prepared in Example 5 was weighed and added to the solid-phase reaction column. The resin was washed twice with DMF, and swollen in DMF for 30 min. 32.22 g Boc-His(Boc)-OH.DCHA (60 mmol), 22.81 g HATU (60 mmol), 9.80 g HOAt (72 mmol) were added to the resin followed by addition of 500 ml NMP solution. After stirring for 5 min, 20.86 ml DIPEA (120 mmol) was added dropwise, and reaction was performed at 0° C. for 3 h. The endpoint of the reaction was determined by ninhydrin test, in which the colorless and transparent resin indicated a complete reaction; while the coloring developed in the resin indicated an incomplete reaction, for which a further hour of coupling reaction was required.

Example 9

Synthesis of the Peptide-Resin of SEQ ID No. 2 by In-Situ Coupling Method Using Boc-His(Boc)-OH.DCHA and the Peptide-Resin of SEQ ID No. 1

15 mmol of the peptide-resin of SEQ ID No. 1 prepared in Example 6 was weighed and added to the solid-phase reaction column. The resin was washed twice with DMF, and swollen in DMF for 30 min. 32.22 g Boc-His(Boc)-OH.DCHA (60 mmol), 22.81 g HATU (60 mmol), 9.80 g HOAt (72 mmol) were added to the resin followed by addition of 500 ml DCM solution. After stirring for 5 min, 15.86 ml TMP (120 mmol) was added dropwise, and reaction was performed at 0° C. for 3 h. The endpoint of the reaction was determined by ninhydrin test, in which the colorless and transparent resin indicated a complete reaction; while the coloring developed in the resin indicated an incomplete reaction, for which a further hour of coupling reaction was required.

Example 10

Synthesis of the Peptide-Resin of SEQ ID No. 2 by In-Situ Coupling Method Using Boc-His(Boc)-OH.DCHA and the Peptide-Resin of SEQ ID No. 1

15 mmol of the peptide-resin of SEQ ID No. 1 prepared in Example 4 was weighed and added to the solid-phase reaction column. The resin was washed twice with DMF, and swollen in DMF for 30 min. 32.22 g Boc-His(Boc)-OH.DCHA (60 mmol), 22.81 g HATU (60 mmol), 9.80 g HOAt (72 mmol) were added to the resin followed by addition of 500 ml DMF/DCM (1:1) solution. After stirring for 5 min, 15.86 ml TMP (120 mmol) was added dropwise, and reaction was performed at 0° C. for 3 h. The endpoint of the reaction was determined by ninhydrin test, in which the colorless and transparent resin indicated a complete reaction; while the coloring developed in the resin indicated an incomplete reaction, for which a further hour of coupling reaction was required.

Example 11

Synthesis of the Peptide-Resin of SEQ ID No. 2 by In-Situ Coupling Method Using Boc-His(Boc)-OH.DCHA and the Peptide-Resin of SEQ ID No. 1

15 mmol of the peptide-resin of SEQ ID No. 1 prepared in Example 6 was weighed and added to the solid-phase reaction column. The resin was washed twice with DMF, and swollen in DMF for 30 min. 32.22 g Boc-His(Boc)-OH.DCHA (60 mmol), 22.81 g HATU (60 mmol), 9.80 g HOAt (72 mmol) were added to the resin followed by addition of 500 ml NMP solution. After stirring for 5 min, 15.86 ml TMP (120 mmol) was added dropwise, and reaction was performed at 25° C. for 2 h. The endpoint of the reaction was determined by ninhydrin test, in which the colorless and transparent resin indicated a complete reaction; while the coloring developed in the resin indicated an incomplete reaction, for which a further hour of coupling reaction was required.

Example 12

Synthesis of the Peptide-Resin of SEQ ID No. 2 by In-Situ Coupling Method Using Boc-His(Boc)-OH.DCHA and the Peptide-Resin of SEQ ID No. 1

15 mmol of the peptide-resin of SEQ ID No. 1 prepared in Example 5 was weighed and added to the solid-phase reaction column. The resin was washed twice with DMF, and swollen in DMF for 30 min. 32.22 g Boc-His(Boc)-OH.DCHA (60 mmol), 22.81 g HATU (60 mmol), 9.80 g HOAt (72 mmol) were added to the resin followed by addition of 500 ml DCM solution. After stirring for 5 min, 15.86 ml TMP (120 mmol) was added dropwise, and reaction was performed at 25° C. for 2 h. The endpoint of the reaction was determined by ninhydrin test, in which the colorless and transparent resin indicated a complete reaction; while the coloring developed in the resin indicated an incomplete reaction, for which a further hour of coupling reaction was required.

Example 13

Synthesis of the Peptide-Resin of SEQ ID No. 2 by In-Situ Coupling Method Using Boc-His(Boc)-OH.DCHA and the Peptide-Resin of SEQ ID No. 1

15 mmol of the peptide-resin of SEQ ID No. 1 prepared in Example 6 was weighed and added to the solid-phase reaction column. The resin was washed twice with DMF, and swollen in DMF for 30 min. 32.22 g Boc-His(Boc)-OH.DCHA (60 mmol), 22.81 g HATU (60 mmol), 9.80 g HOAt (72 mmol) were added to the resin followed by addition of 500 ml DMF/DCM (1:1) solution. After stirring for 5 min, 15.86 ml TMP (120 mmol) was added dropwise, and reaction was performed at 25° C. for 2 h. The endpoint of the reaction was determined by ninhydrin test, in which the colorless and transparent resin indicated a complete reaction; while the coloring developed in the resin indicated an incomplete reaction, for which a further hour of coupling reaction was required.

Example 14

Synthesis of the Peptide-Resin of SEQ ID No. 2 by In-Situ Coupling Method Using Boc-His(Boc)-OH.DCHA and the Peptide-Resin of SEQ ID No. 1

15 mmol of the peptide-resin of SEQ ID No. 1 prepared in Example 5 was weighed and added to the solid-phase reaction column. The resin was washed twice with DMF, and swollen in DMF for 30 min. 32.22 g Boc-His(Boc)-OH.DCHA (60 mmol), 22.81 g HATU (60 mmol), 9.80 g HOAt (72 mmol) were added to the resin followed by addition of 500 ml NMP/DCM (1:1) solution. After stirring for 5 min, 15.86 ml TMP (120 mmol) was added dropwise, and reaction was performed at 25° C. for 2 h. The endpoint of the reaction was determined by ninhydrin test, in which the colorless and transparent resin indicated a complete reaction; while the coloring developed in the resin indicated an incomplete reaction, for which a further hour of coupling reaction was required.

Example 15

Synthesis of the Peptide-Resin of SEQ ID No. 2 by In-Situ Coupling Method Using Boc-His(Boc)-OH.DCHA and the Peptide-Resin of SEQ ID No. 1

15 mmol of the peptide-resin of SEQ ID No. 1 prepared in Example 4 was weighed and added to the solid-phase reaction column. The resin was washed twice with DMF, and swollen in DMF for 30 min. 32.22 g Boc-His(Boc)-OH.DCHA (60 mmol), 22.81 g HATU (60 mmol), 9.80 g HOAt (72 mmol) were added to the resin followed by addition of 500 ml NMP solution. After stirring for 5 min, 15.86 ml TMP (120 mmol) was added dropwise, and reaction was performed at 30° C. for 2 h. The endpoint of the reaction was determined by ninhydrin test, in which the colorless and transparent resin indicated a complete reaction; while the coloring developed in the resin indicated an incomplete reaction, for which a further hour reaction was required. Such criteria were applied to the endpoint determination by ninhydrin test herein below.

Example 16

Synthesis of the Peptide-Resin of SEQ ID No. 2 by In-Situ Coupling Method Using Boc-His(Boc)-OH.DCHA and the Peptide-Resin of SEQ ID No. 1

15 mmol of the peptide-resin of SEQ ID No. 1 prepared in Example 5 was weighed and added to the solid-phase reaction column. The resin was washed twice with DMF, and swollen in DMF for 30 min. 32.22 g Boc-His(Boc)-OH.DCHA (60 mmol), 22.81 g HATU (60 mmol), 9.80 g HOAt (72 mmol) were added to the resin followed by addition of 500 ml DCM solution. After stirring for 5 min, 15.86 ml TMP (120 mmol) was added dropwise, and reaction was performed at 30° C. for 2 h. The endpoint of the reaction was determined by ninhydrin test, in which the colorless and transparent resin indicated a complete reaction; while the coloring developed in the resin indicated an incomplete reaction, for which a further hour of coupling reaction was required.

Example 17

Synthesis of the Peptide-Resin of SEQ ID No. 2 by In-Situ Coupling Method Using Boc-His(Boc)-OH.DCHA and the Peptide-Resin of SEQ ID No. 1

15 mmol of the peptide-resin of SEQ ID No. 1 prepared in Example 4 was weighed and added to the solid-phase reaction column. The resin was washed twice with DMF, and swollen in DMF for 30 min. 32.22 g Boc-His(Boc)-OH.DCHA (60 mmol), 22.81 g HATU (60 mmol), 9.80 g HOAt (72 mmol) were added to the resin followed by addition of 500 ml DMF solution. After stirring for 5 min, 15.86 ml TMP (120 mmol) was added dropwise, and reaction was performed at 30° C. for 2 h. The endpoint of the reaction was determined by ninhydrin test, in which the colorless and transparent resin indicated a complete reaction; while the coloring developed in the resin indicated an incomplete reaction, for which a further hour of coupling reaction was required.

Example 18

Synthesis of the Peptide-Resin of SEQ ID No. 2 by In-Situ Coupling Method Using Boc-His(Boc)-OH.DCHA and the Peptide-Resin of SEQ ID No. 1

15 mmol of the peptide-resin of SEQ ID No. 1 prepared in Example 6 was weighed and added to the solid-phase reaction column. The resin was washed twice with DMF, and swollen in DMF for 30 min. 32.22 g Boc-His(Boc)-OH.DCHA (60 mmol), 22.81 g HATU (60 mmol), 9.80 g HOAt (72 mmol) were added to the resin followed by addition of 500 ml DMF/DMF (1:1) solution. After stirring for 5 min, 15.86 ml TMP (120 mmol) was added dropwise, and reaction was performed at 30° C. for 2 h. The endpoint of the reaction was determined by ninhydrin test, in which the colorless and transparent resin indicated a complete reaction; while the coloring developed in the resin indicated an incomplete reaction, for which a further hour of coupling reaction was required.

Example 19

Synthesis of the Peptide-Resin of SEQ ID No. 2 by Pre-Activation Coupling Method Using Boc-His(Boc)-OH.DCHA and the Peptide-Resin of SEQ ID No. 1

15 mmol of the peptide-resin of SEQ ID No. 1 prepared in Example 6 was weighed and added to the solid-phase reaction column. The resin was washed twice with DMF, and swollen in DMF for 30 min. 32.22 g Boc-His(Boc)-OH.DCHA (60 mmol), 22.81 g HATU (60 mmol), 9.80 g HOAt (72 mmol) were added to the resin and dissolved in 500 ml DMF. After activation for 5 min by adding 15.86 ml TMP (120 mmol) in an ice water bath, the mixed solution was added to the reaction column and reaction was performed at room temperature for 2 h. The endpoint of the reaction was determined by ninhydrin test, in which the colorless and transparent resin indicated a complete reaction; while the coloring developed in the resin indicated an incomplete reaction, for which a further hour of coupling reaction was required.

Example 20

Synthesis of the Peptide-Resin of SEQ ID No. 2 by In-Situ Coupling Method Using Fmoc-His(Boc)-OH.DCHA and the Peptide-Resin of SEQ ID No. 1

15 mmol of the peptide-resin of SEQ ID No. 1 prepared in Example 4 was weighed and added to the solid-phase reaction column. The resin was washed twice with DMF, and swollen in DMF for 30 min. 34.56 g Fmoc-His(Boc)-OH.CHA (60 mmol), 22.81 g HATU (60 mmol), 9.80 g HOAt (72 mmol) were added to the resin followed by addition of 500 ml NMP solution. After stirring for 5 min, 15.86 ml TMP (120 mmol) was added dropwise, and reaction was performed at 0° C. for 3 h. The endpoint of the reaction was determined by ninhydrin test, in which the colorless and transparent resin indicated a complete reaction; while the coloring developed in the resin indicated an incomplete reaction, for which a further hour of coupling reaction was required. The Fmoc protection was removed by DBLK, and the resin was then washed with DMF for 6 times. The resin was tested by ninhydrin test, in which the removal of Fmoc was indicated by the coloring developed in the resin.

Example 21

Synthesis of the Peptide-Resin of SEQ ID No. 2 by In-Situ Coupling Method Using Fmoc-His(Bum)-OH and the Peptide-Resin of SEQ ID No. 1

15 mmol of the peptide-resin of SEQ ID No. 1 prepared in Example 5 was weighed and added to the solid-phase reaction column. The resin was washed twice with DMF, and swollen in DMF for 30 min. 27.81 g Fmoc-His(Bum)-OH (60 mmol), 22.81 g HATU (60 mmol), 9.80 g HOAt (72 mmol) were added to the resin followed by addition of 500 ml NMP solution. After stirring for 5 min, 15.86 ml TMP (120 mmol) was added dropwise, and reaction was performed at 0° C. for 3 h. The endpoint of the reaction was determined by ninhydrin test, in which the colorless and transparent resin indicated a complete reaction; while the coloring developed in the resin indicated an incomplete reaction, for which a further hour of coupling reaction was required. The Fmoc protection was removed by DBLK, and the resin was then washed with DMF for 6 times. The resin was tested by ninhydrin test, in which the removal of Fmoc was indicated by the coloring developed in the resin.

Example 22

Synthesis of the Peptide-Resin of SEQ ID No. 2 by In-Situ Coupling Method Using Fmoc-His(mmt)-OH and the Peptide-Resin of SEQ ID No. 1

15 mmol of the peptide-resin of SEQ ID No. 1 prepared in Example 5 was weighed and added to the solid-phase reaction column. The resin was washed twice with DMF, and swollen in DMF for 30 min. 38.98 g Fmoc-His(mmt)-OH (60 mmol), 22.81 g HATU (60 mmol), 9.80 g HOAt (72 mmol) were added to the resin followed by addition of 500 ml NMP solution. After stirring for 5 min, 15.86 ml TMP (120 mmol) was added dropwise, and reaction was performed at 0° C. for 3 h. The endpoint of the reaction was determined by ninhydrin test, in which the colorless and transparent resin indicated a complete reaction; while the coloring developed in the resin indicated an incomplete reaction, for which a further hour of coupling reaction was required. The Fmoc protection was removed by DBLK, and the resin was then washed with DMF for 6 times. The resin was tested by ninhydrin test, in which the removal of Fmoc was indicated by the coloring developed in the resin.

Example 23

Synthesis of the Peptide-Resin of SEQ ID No. 2 by In-Situ Coupling Method Using Fmoc-His(mtt)-OH and the Peptide-Resin of SEQ ID No. 1

15 mmol of the peptide-resin of SEQ ID No. 1 prepared in Example 4 was weighed and added to the solid-phase reaction column. The resin was washed twice with DMF, and swollen in DMF for 30 min. 38.02 g Fmoc-His(mtt)-OH (60 mmol), 22.81 g HATU (60 mmol), 9.80 g HOAt (72 mmol) were added to the resin followed by addition of 500 ml NMP solution. After stirring for 5 min, 15.86 ml TMP (120 mmol) was added dropwise, and reaction was performed at 0° C. for 3 h. The endpoint of the reaction was determined by ninhydrin test, in which the colorless and transparent resin indicated a complete reaction; while the coloring developed in the resin indicated an incomplete reaction, for which a further hour of coupling reaction was required. The Fmoc protection was removed by DBLK, and the resin was then washed with DMF for 6 times. The resin was tested by ninhydrin test, in which the removal of Fmoc was indicated by the coloring developed in the resin.

Example 24

Synthesis of the Peptide-Resin of SEQ ID No. 2 by In-Situ Coupling Method Using Boc-His(Trt)-OH and the Peptide-Resin of SEQ ID No. 1

15 mmol of the peptide-resin of SEQ ID No. 1 prepared in Example 6 was weighed and added to the solid-phase reaction column. The resin was washed twice with DMF, and swollen in DMF for 30 min. 29.86 g Boc-His(Trt)-OH (60 mmol), 22.81 g HATU (60 mmol), 9.80 g HOAt (72 mmol) were added to the resin followed by addition of 500 ml NMP solution. After stirring for 5 min, 15.86 ml TMP (120 mmol) was added dropwise, and reaction was performed at 0° C. for 3 h. The endpoint of the reaction was determined by ninhydrin test, in which the colorless and transparent resin indicated a complete reaction; while the coloring developed in the resin indicated an incomplete reaction, for which a further hour of coupling reaction was required.

Example 25

Synthesis of the Peptide-Resin of SEQ ID No. 2 by In-Situ Coupling Method Using Boc-His(Bum)-OH and the Peptide-Resin of SEQ ID No. 1

15 mmol of the peptide-resin of SEQ ID No. 1 prepared in Example 4 was weighed and added to the solid-phase reaction column. The resin was washed twice with DMF, and swollen in DMF for 30 min. 20.49 g Boc-His(Bum)-OH (60 mmol), 22.81 g HATU (60 mmol), 9.80 g HOAt (72 mmol) were added to the resin followed by addition of 500 ml NMP solution. After stirring for 5 min, 15.86 ml TMP (120 mmol) was added dropwise, and reaction was performed at 0° C. for 3 h. The endpoint of the reaction was determined by ninhydrin test, in which the colorless and transparent resin indicated a complete reaction; while the coloring developed in the resin indicated an incomplete reaction, for which a further hour of coupling reaction was required.

Example 26

Synthesis of the Peptide-Resin of SEQ ID No. 2 by In-Situ Coupling Method Using Boc-His(mmt)-OH and the Peptide-Resin of SEQ ID No. 1

15 mmol of the peptide-resin of SEQ ID No. 1 prepared in Example 5 was weighed and added to the solid-phase reaction column. The resin was washed twice with DMF, and swollen in DMF for 30 min. 31.66 g Boc-His(mmt)-OH (60 mmol), 22.81 g HATU (60 mmol), 9.80 g HOAt (72 mmol) were added to the resin followed by addition of 500 ml NMP solution. After stirring for 5 min, 15.86 ml TMP (120 mmol) was added dropwise, and reaction was performed at 0° C. for 3 h. The endpoint of the reaction was determined by ninhydrin test, in which the colorless and transparent resin indicated a complete reaction; while the coloring developed in the resin indicated an incomplete reaction, for which a further hour of coupling reaction was required.

Example 27

Synthesis of the Peptide-Resin of SEQ ID No. 2 by In-Situ Coupling Method Using Boc-His(mtt)-OH and the Peptide-Resin of SEQ ID No. 1

15 mmol of the peptide-resin of SEQ ID No. 1 prepared in Example 6 was weighed and added to the solid-phase reaction column. The resin was washed twice with DMF, and swollen in DMF for 30 min. 30.70 g Boc-His(mtt)-OH (60 mmol), 22.81 g HATU (60 mmol), 9.80 g HOAt (72 mmol) were added to the resin followed by addition of 500 ml NMP solution. After stirring for 5 min, 15.86 ml TMP (120 mmol) was added dropwise, and reaction was performed at 0° C. for 3 h. The endpoint of the reaction was determined by ninhydrin test, in which the colorless and transparent resin indicated a complete reaction; while the coloring developed in the resin indicated an incomplete reaction, for which a further hour of coupling reaction was required.

Example 28

Synthesis of the Peptide-Resin of SEQ ID No. 2 by In-Situ Coupling Method Using Trt-His(Trt)-OH and the Peptide-Resin of SEQ ID No. 1

15 mmol of the peptide-resin of SEQ ID No. 1 prepared in Example 5 was weighed and added to the solid-phase reaction column. The resin was washed twice with DMF, and swollen in DMF for 30 min. 38.39 g Trt-His(Trt)-OH (60 mmol), 22.81 g HATU (60 mmol), 9.80 g HOAt (72 mmol) were added to the resin followed by addition of 500 ml NMP solution. After stirring for 5 min, 15.86 ml TMP (120 mmol) was added dropwise, and reaction was performed at 0° C. for 3 h. The endpoint of the reaction was determined by ninhydrin test, in which the colorless and transparent resin indicated a complete reaction; while the coloring developed in the resin indicated an incomplete reaction, for which a further hour of coupling reaction was required.

Example 29

Cleavage of Exenatide-Resin 100 g peptide-resin obtained in any one of Examples 7-28 was placed in a cleavage reactor. Subsequently, the cleaving agent TFA:PhSMe:EDT:TIS:$H_2O$:phenol=80:5:5:5:3:2 (v/v) was added in a ratio of 10 ml/g resin and stirred at room temperature for 2 h. The reactants were filtered by a sintered filter funnel and the filtrate was collected. The resin was washed by a small amount of TFA for 3 times and the filtrates were combined. The filtrate was precipitated by adding ice cooled absolute ethyl ether (in an amount of 100 ml/g resin). The precipitate was then centrifuged, and the pellet was washed by anhydrous ethyl ether for 3 times and dried under vacuum to obtain white powder, i.e., crude exenatide.

Example 30

Cleavage of Exenatide-Resin 100 g peptide-resin obtained in any one of Example 7-28 was placed in a cleavage reactor. Subsequently, the cleaving agent TFA:PhSMe:EDT:TIS:$H_2O$:Phenol=85:4:4:4:2:1 (v/v) was added in a ratio of 10 ml/g resin and stirred at room temperature for 2 h. The reactants were filtered by a sintered filter funnel and the filtrate was collected. The resin was washed by a small amount of TFA for 3 times and the filtrates were combined. The filtrate was precipitated by adding ice cooled absolute ethyl ether (in an amount of 100 ml/g resin). The precipitate was then centrifuged, and the pellet was washed by anhydrous ethyl ether for 3 times and dried under vacuum to obtain white powder, i.e., crude exenatide.

Example 31

Cleavage of Exenatide-Resin 100 g peptide-resin obtained in any one of Example 7-28 was placed in a cleavage reactor. Subsequently, the cleaving agent TFA:PhSMe:EDT:TIS:$H_2O$:phenol=81.5:5:5:5:2.5:1 (v/v) was added in a ratio of 10 ml/g resin and stirred at room temperature for 2 h. The reactants were filtered by a sintered filter funnel and the filtrate was collected. The resin was washed by a small amount of TFA for 3 times and the filtrates were combined. The filtrate was precipitated by adding ice cooled absolute ethyl ether (in an amount of 100 ml/g resin). The precipitate was then centrifuged, and the pellet was washed by anhydrous ethyl ether for 3 times and dried under vacuum to obtain white powder, i.e., crude exenatide.

Example 32

Preparation of Purified Exenatide Acetate 20.0 g crude exenatide obtained in any one of Example 29-31 was weighed and dissolved in 2000 ml water. The solution was purified by Waters 2545 RP-HPLC system equipped with 50×250 mm reverse phase C18 column using conventional 0.2% TFA/acetonitrile solution as mobile phase. The eluant was detected at a wavelength of 230 nm and fractions of target peak were collected, to obtain purified peptide with a purity greater than 98.5%. In Waters 2545 RP-HPLC system equipped with 50×250 mm reverse-phase C18 column, the purified peptide solution was converted into its salt using 0.2% acetic acid solution/acetonitrile as mobile phase. The fractions of target peak were collected and concentrated by rotary evaporation. After freeze-drying, 4.2 g purified exenatide acetate was obtained with an HPLC purity of 98.5%. The content of D-His-exenatide in the polished exenatide was less than 0.5%, as detected by SCX-HPLC method.

Example 33

Large-Scale Preparation of Purified Exenatide Acetate 1000 g Rink Amide-MBHA resin was weighed and added to the solid-phase reaction column and was washed with DMF twice. After the resin was swollen in DMF for 30 minutes, the Fmoc protection was removed by DBLK and the resin was washed by DMF for 6 times. The resin was tested by ninhydrin test, in which the removal of Fmoc was indicated by the coloring developed in the resin. 92.0 g Fmoc-Ser(tBu)-OH (240 mmol) and 38.9 g HOBt (288 mmol) were weighed and dissolved in a mixed solution of DCM and DMF in a volume ratio of 1:1. After activation for 3 min by adding 45 ml DIC (288 mmol) in an ice water bath, the solution was added to the solid-phase reaction column and reaction was performed at room temperature for 2 h. The resin was washed with DMF for 3 times, the blocking solution (pyridine/acetic anhydride=1:1) was added for blocking for 2 h. The resin was washed with each of DMF and DCM for 4 times, shrunk in methanol and methanol was removed to dry by sucking, Fmoc-Ser(tBu)-Rink Amide-MBHA resin was obtained. The substitution degree was determined to be 0.189 mmol/g.

1005.3 g (190 mmol) Fmoc-Ser(tBu)-Rink Amide-MBHA resin with a substitution degree of 0.189 mmol/g was weighed and added to the solid-phase reaction column. Subsequently, the resin was washed twice using DMF, and swollen in DMF for 30 min. Fmoc protection was removed by DBLK, and the resin was then washed for 6 times using DMF. The resin was tested by ninhydrin test, in which the removal of Fmoc was indicated by the coloring developed in the resin. 256.42 g Fmoc-Pro-OH (760 mmol) and 123.21 g HOBt (912 mmol) were weighed and dissolved in a mixed solution of DCM and DMF in a volume ratio of 1:1. After activation for 3 min by adding 142.57 ml DIC (912 mmol) in an ice water bath, the solution was added to the solid-phase reaction column and reaction was performed at room temperature for 2 h. The endpoint of the reaction was determined by ninhydrin test, in which the colorless and transparent resin indicated a complete reaction; while the coloring developed in the resin indicated an incomplete reaction, for which a further hour reaction was required. Such criteria were applied to the endpoint determination by ninhydrin test herein below. The coupling of 2-39 fragment was accomplished sequentially from C-terminal to N-terminal according to the backbone sequence of exenatide by repeating the above step of removing the Fmoc protection and the step of coupling with corresponding amino acids added. 408.12 g Boc-His(Boc)-OH.DCHA (760 mmol), 288.95 g HATU (760 mmol), 124.12 g HOAt (912 mmol) were added to the resin followed by addition of 5000 ml NMP/DCM (1:1) solution. After stirring for 5 min, 200.9 ml TMP (1520 mmol) was added dropwise, and reaction was performed at 0° C. for 3 h. The endpoint of the reaction was determined by ninhydrin test, in which the colorless and transparent resin indicated a complete reaction; while the coloring developed in the resin indicated an incomplete reaction, for which a further hour of coupling reaction was required. After the reaction was finished, the resin was shrunk in methanol and dried under vacuum over night, resulting in 2029.6 g peptide-resin of SEQ ID No. 1 by weighing.

2029.6 g peptide-resin of SEQ ID No. 1 was placed in a cleavage reactor. Subsequently, the cleaving agent TFA:PhSMe:EDT:TIS:$H_2O$:phenol=81.5:5:5:5:2.5:1 (v/v) was added in a ratio of 10 ml/g resin and stirred at room temperature for 2 h. The reactants were filtered by a sintered filter funnel and the filtrate was collected. The resin was washed by a small amount of TFA for 3 times and the filtrates were combined. The filtrate was precipitated by ice cooled absolute ethyl ether (in an amount of 100 ml/g resin). The precipitate was then centrifuged, and the pellet was washed by anhydrous ethyl ether for 3 times and dried under vacuum to obtain 836.97 g white powder, i.e., crude exenatide, with a weight yield of 105.2% and a crude peptide purity of 55.9%.

After the crude exenatide was converted to salt via purification, 173.68 g purified exenatide was finally obtained with an HPLC purity of 98.9%, wherein the content of D-His-exenatide was 0.19%, as determined by SCX-HPLC.

Example 34

Control Group 10 g Fmoc-Ser(tBu)-Rink Amide-MBHA resin with a substitution degree of 0.15 mmol/g was weighed and added the solid-phase reaction column. Subsequently, the resin was washed twice using DMF, and swollen in DMF for 30 min. Fmoc protection was removed by DBLK, and the resin was then washed for 6 times using DMF. The resin was tested by ninhydrin test, in which the removal of Fmoc was indicated by the coloring developed in the resin. 2.02 g Fmoc-Pro-OH (6 mmol) and 0.97 g HOBt (7.2 mmol) were weighed and dissolved in a mixed solution of DCM and DMF in a volume ratio of 1:1. After activation for 3 min by adding 1.13 ml DIC (7.2 mmol) in an ice water bath, the solution was added to the solid-phase reaction column and reaction was performed at room temperature for 2 h. The endpoint of the reaction was determined by ninhydrin test, in which the colorless and transparent resin indicated a complete reaction; while the coloring developed in the resin indicated an incomplete reaction, for which a further hour reaction was required. Such criteria were applied to the endpoint determination by ninhydrin test herein below. The coupling of the rest amino acids was accomplished sequentially from C-terminal to N-terminal according to the backbone sequence of exenatide by repeating the above step of removing the Fmoc protection and the step of coupling with corresponding amino acid added, wherein the amino acid at position 1 at N-terminal was Fmoc-His(Trt)-OH. After the reaction was finished, the resin was shrunk in methanol and dried under vacuum over night, resulting in 19.3 g exenatide-resin by weighing.

The resultant peptide-resin was added to 193 ml cleaving agent TFA:PhSMe:EDT:TIS:$H_2O$:phenol=85:4:4:4:2:1 (v/v), and stirred at room temperature for 2 h. The reactants were filtered by a sintered filter funnel and the filtrate was collected. The resin was washed by a small amount of TFA for 3 times and the filtrates were combined. The filtrate was precipitated by ice cooled absolute ethyl ether (in an amount of 100 ml/g resin). The precipitate was then centrifuged, and the pellet was washed by anhydrous ether for 3 times and dried under vacuum to result in white powdery solid, i.e., crude exenatide.

The obtained crude exenatide was converted into its salt by purification using RP-HPLC, resulting in 1.75 g exenatide acetate with an HPLC purity of 94.3%.

Figure 1:
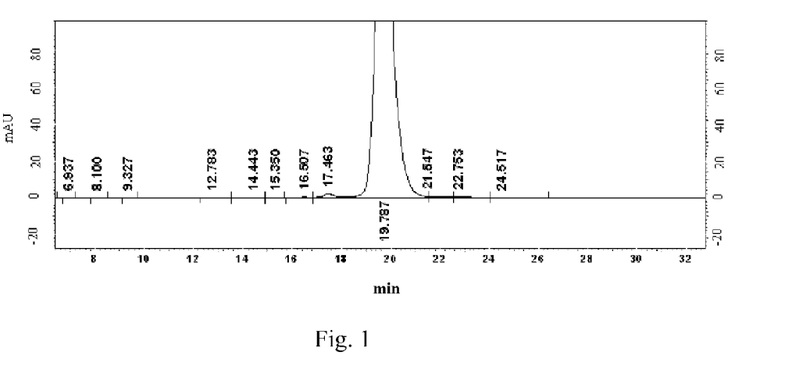
FIG. 1 is the HPLC chromatogram of the purified peptide prepared in the control group in Example 34.

Based on the detection using SCX-HPLC, the liquid chromatogram was shown in FIG. 1, wherein RT21.523 indicated D-His-exenatide with a content of 2.73%.

Test Group:

1000 g Rink Amide-MBHA resin was weighed and added to the solid-phase reaction column followed by washing with DMF twice. After the resin was swollen in DMF for 30 minutes, the Fmoc protection was removed by DBLK and the resin was washed by DMF for 6 times. The resin was tested by ninhydrin test, in which the removal of Fmoc was indicated by the coloring developed in the resin. 92.0 g Fmoc-Ser(tBu)-OH (240 mmol) and 38.9 g HOBt (288 mmol) were weighed and dissolved in a mixed solution of DCM and DMF in a volume ratio of 1:1. After activation for 3 min by adding 45 ml DIC (288 mmol) in an ice water bath, the solution was added to the solid-phase reaction column and reaction was performed at room temperature for 2 h. The resin was washed with DMF for 3 times, the blocking solution (pyridine/acetic anhydride=1:1) was added for blocking for 2 h. The resin was washed with each of DMF and DCM for 4 times, shrunk in methanol and methanol was removed to dry by sucking, Fmoc-Ser(tBu)-Rink Amide-MBHA resin was obtained. The substitution degree was determined to be 0.193 mmol/g.

984.5 g (190 mmol) Fmoc-Ser(tBu)-Rink Amide-MBHA resin with a substitution degree of 0.193 mmol/g was weighed and added to the solid-phase reaction column. Subsequently, the resin was washed twice using DMF, and swollen in DMF for 30 min. Fmoc protection was removed by DBLK, and the resin was then washed for 6 times using DMF. The resin was tested by ninhydrin test, in which the removal of Fmoc was indicated by the coloring developed in the resin. 256.42 g Fmoc-Pro-OH (760 mmol) and 123.21 g HOBt (912 mmol) were weighed and dissolved in a mixed solution of DCM and DMF in a volume ratio of 1:1. After activation for 3 min by adding 142.57 ml DIC (912 mmol) in an ice water bath, the solution was added to the solid-phase reaction column and reaction was performed at room temperature for 2 h. The endpoint of the reaction was determined by ninhydrin test, in which the colorless and transparent resin indicated a complete reaction; while the coloring developed in the resin indicated an incomplete reaction, for which a further hour reaction was required. Such criteria were applied to the endpoint determination by ninhydrin test herein below. The coupling of 2-39 fragment was accomplished sequentially from C-terminal to N-terminal according to the backbone sequence of exenatide by repeating the above step of removing the Fmoc protection and the step of coupling with corresponding amino acid added. 408.12 g Boc-His(Boc)-OH.DCHA (760 mmol), 288.95 g HATU (760 mmol), 124.12 g HOAt (912 mmol) were added to the resin followed by addition of 5000 ml NMP/DCM (1:1) solution. After stirring for 5 min, 200.9 ml TMP (1520 mmol) was added dropwise, and reaction was performed at 0° C. for 3 h. The endpoint of the reaction was determined by ninhydrin test, in which the colorless and transparent resin indicated a complete reaction; while the coloring developed in the resin indicated an incomplete reaction, for which a further hour of coupling reaction was required. After the reaction was finished, the resin was shrunk in methanol and dried under vacuum over night, resulting in 1998.7 g peptide-resin of SEQ ID No. 1 by weighing.

1998.7 g peptide-resin of SEQ ID No. 1 was placed in a cleavage reactor. Subsequently, the cleaving agent (TFA:PhSMe:EDT:TIS:$H_2$O:phenol=81.5:5:5:5:2.5:1 v/v) was added in a ratio of 10 ml/g resin and stirred at room temperature for 2 h. The reactants were filtered by a sintered filter funnel and the filtrate was collected. The resin was washed by a small amount of TFA for 3 times and the filtrates were combined. The filtrate was precipitated by ice cooled absolute ethyl ether (in an amount of 100 ml/g resin). The precipitate was then centrifuged, and the pellet was washed by anhydrous ether for 3 times and dried under vacuum to obtain 846.9 g white powder, i.e., crude exenatide, with a weight yield of 106.5% and a crude peptide purity of 56.7%.

Figure 2:
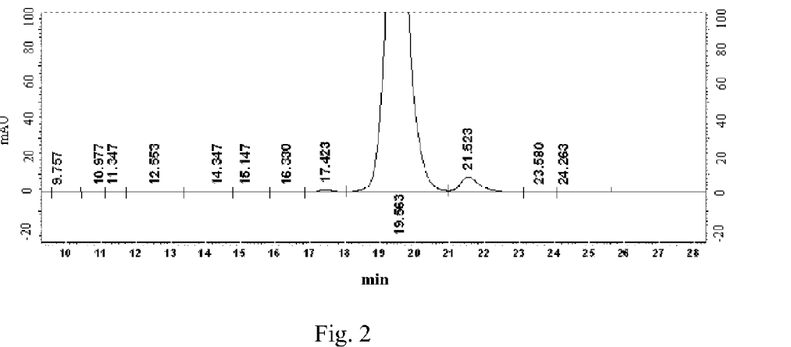
FIG. 2 is the HPLC chromatogram of the purified peptide prepared in the test group in Example 34.

The obtained crude exenatide was converted into its salt by purification using RP-HPLC, resulting in 176.84 g exenatide acetate with an HPLC purity of 99.01%. Based on the detection using SCX-HPLC, typical chromatogram was shown in FIG. 2 for the resultants obtained by the method provided herein, wherein RT21.547 indicated D-His-exenatide with the content of 0.20%.

A method for the preparation of exenatide provided by the present invention has been described in detail above. The principle and practice of the present invention has been illustrated by specific Examples above. Description of the Examples is only used to facilitate the understanding of the methods and key concepts of the present invention. It should be noted that several improvements and modifications can be made to the present invention by the person of ordinary skill in the art without departing from the principles of the present invention. These improvements and modifications should also be regarded as in the scope of the claims of the present invention.

---

The invention claimed is:

1. A method for the preparation of exenatide comprising:
   (a) obtaining a serine-resin by a first coupling between serine and resin;
   (b) obtaining a peptide-resin of SEQ ID NO: 1 by a secondary coupling of said serine-resin sequentially with amino acids; and
   (c) obtaining a peptide-resin of SEQ ID NO: 2 by a third coupling between the protective group-containing histidine or a salt thereof with said peptide-resin of SEQ ID No. 1, and exenatide is finally obtained after cleavage and purification wherein the protective group-containing histidine or a salt thereof in step (c) has the structure as shown in formula IV:

Boc-His(Boc)-OH.DCHA    (Formula IV), wherein step (c) comprises obtaining exenatide-resin in a solvent in the presence of a coupling agent and an organic base, wherein the coupling agent is HATU and HOAt.

2. The preparation method according to claim 1, wherein the third coupling is pre-activation coupling or in-situ coupling.

3. The preparation method according to claim 1, wherein the organic base is DIPEA or TMP.

4. The preparation method according to claim 1, wherein the solvent is one of NMP, DMF and DCM, or a mixture of two or more thereof.

5. The preparation method according to claim 1, wherein the cleaving agent is a mixture of TFA, PhSMe, EDT, TIS, water and phenol.

6. The preparation method according to claim 5, wherein the volume ratio of TFA, PhSMe, EDT, TIS, water and phenol in the cleaving agent is 80-85:2-5:2-5:2-5:0-3:0-2.

* * * * *

SEQUENCE LISTING

```
<160> NUMBER OF SEQ ID NOS: 2

<210> SEQ ID NO 1
<211> LENGTH: 38
<212> TYPE: PRT
<213> ORGANISM: Artificial Sequence
<220> FEATURE:
<223> OTHER INFORMATION: Synthetic primer

<400> SEQUENCE: 1

Gly Glu Gly Thr Phe Thr Ser Asp Leu Ser Lys Gln Glu Glu Glu Glu
1               5                   10                  15

Ala Val Arg Leu Phe Ile Glu Trp Leu Leu Asn Gly Gly Pro Ser Ser
            20                  25                  30

Gly Ala Pro Pro Pro Ser
        35

<210> SEQ ID NO 2
<211> LENGTH: 39
<212> TYPE: PRT
<213> ORGANISM: Artificial Sequence
<220> FEATURE:
<223> OTHER INFORMATION: Synthetic peptide

<400> SEQUENCE: 2
```

```
His Gly Glu Gly Thr Phe Thr Ser Asp Leu Ser Lys Gln Glu Glu Glu
1               5                   10                  15

Glu Ala Val Arg Leu Phe Ile Glu Trp Leu Leu Asn Gly Gly Pro Ser
            20                  25                  30

Ser Gly Ala Pro Pro Pro Ser
        35
```

UNITED STATES PATENT AND TRADEMARK OFFICE
CERTIFICATE OF CORRECTION

PATENT NO. : 9,637,517 B2
APPLICATION NO. : 14/371004
DATED : May 2, 2017
INVENTOR(S) : Pengcheng Mi et al.

Page 1 of 1

It is certified that error appears in the above-identified patent and that said Letters Patent is hereby corrected as shown below:

In the Claims

In Claim 1, Column 21, Line 23, delete "purification" and insert --purification,-- therefor.

Signed and Sealed this
Twenty-fifth Day of July, 2017

Joseph Matal
*Performing the Functions and Duties of the*
*Under Secretary of Commerce for Intellectual Property and*
*Director of the United States Patent and Trademark Office*